United States Patent [19]

Picha

[11] Patent Number: 5,540,464
[45] Date of Patent: Jul. 30, 1996

[54] CAPILLARY CONNECTOR

[75] Inventor: Neil R. Picha, Placerville, Calif.

[73] Assignee: J&W Scientific Incorporated, Folsom, Calif.

[21] Appl. No.: 317,966

[22] Filed: Oct. 4, 1994

[51] Int. Cl.$^6$ .................................................. F16L 25/00
[52] U.S. Cl. ...................... 285/328; 285/911; 285/417; 285/915; 285/332; 96/106; 210/198.2; 604/283
[58] Field of Search .................................. 285/328, 417, 285/332, 334.4, 911, 915; 96/101, 105, 106; 210/198.2; 604/905, 283

[56] References Cited

U.S. PATENT DOCUMENTS

| | | | |
|---|---|---|---|
| 4,026,803 | 5/1977 | Abrahams et al. | 210/198.2 |
| 4,083,702 | 4/1978 | Hartigan et al. | 96/106 |
| 4,313,828 | 2/1982 | Brownlef | 285/109 |
| 4,529,230 | 7/1985 | Fatula, Jr. . | |
| 4,669,756 | 6/1987 | Cassaday et al. | 96/106 |
| 4,690,437 | 9/1987 | Anderson, Jr. | 785/911 |
| 4,787,656 | 11/1988 | Ryder | 285/911 |
| 4,820,288 | 4/1989 | Isono | 285/169 |
| 4,991,883 | 2/1991 | Worden | 285/334.4 |
| 5,160,178 | 11/1992 | Iwabulni | 285/328 |
| 5,163,722 | 11/1992 | Worden | 285/342 |
| 5,234,235 | 8/1993 | Worden | 285/342 |
| 5,236,688 | 8/1993 | Higdon . | |
| 5,288,113 | 2/1994 | Silvis et al. . | |
| 5,298,225 | 3/1994 | Higdon . | |
| 5,423,581 | 6/1995 | Salyers | 285/159 |

OTHER PUBLICATIONS

"Call for fused silica tubing furnishing tight press–fit connections", Grob et al., Journal of High Resolution Chromatography, vol. 15, Sep. 1992, pp. 613, 614.
"Simple press–fit connectors for flexible fused silica tubing in gas–liquid chromatography", Rohwer et al., Journal of High Resolution Chromatography and Chromatography Communications, vol. 9, May 1986, pp. 295–297.
"Accessories to make your analyses easier" and Use of Supelco butt connectors, Supelco brochure, pp. 338–339.
"Press–tight connectors", Restek catalog, p. 164.
"Non-PAKD Injection", Alltech Associates, p. 7.
"Capillary supplies", Applied Science, p. 120.
"Capillary supplies", Alltech Associates, p.. 121.
"Johanson Manufacturing Corporation, Ferrules & Sleeves", one page.
"Connector geometry raises fiberoptic–link performance", Denny, Laser Focus World, Aug. 1992, pp. 123–130.

Primary Examiner—Eric K. Nicholson
Attorney, Agent, or Firm—Graham & James LLP

[57] ABSTRACT

A capillary column connector assembly includes a pair of body members fabricated from a resilient, inert ceramic having high compressive strength. Each body member has an inwardly tapering longitudinal throughbore within which the end of a capillary column can be inserted by press-fitting. A split sleeve holds the two body members in mutually facing alignment with inner end surfaces in compressed mutual contact. The inner end surfaces are slightly radiussed in order to deform upon compression and provide a fluid-tight seal surrounding the junction between the inner ends of the longitudinal bores, thereby eliminating the need for any separate sealing gasket.

A mechanical assembly comprising an inner spool, an outer housing, a spring, and a bearing-mounted support provide axial compression forces tending to urge the ceramic body members into mutual facing contact with the radiussed surfaces deformed.

36 Claims, 4 Drawing Sheets

CAPILLARY CONNECTOR

BACKGROUND OF THE INVENTION

This invention relates to chromatographic apparatus in general, and more particularly to connectors for capillary columns used in such apparatus.

Chromatographic apparatus used for both gas and liquid chromatography typically employ capillary columns to provide control passage ways for substances to be analyzed. Areas of analytical application include gas chromatography, liquid microbore chromatography, capillary electrophoresis, and supercritical fluid chromatography. In most analytical applications today, glass, metal or flexible fused silica capillary columns are used, and such columns typically have internal dimensions in the range from about 0.02 mm to 0.60 mm and external diameters in the range from about 0.10 mm to 0.80 mm. Polymeric capillaries of similar size are also used on occasion. Frequently, it is necessary to join two pieces of capillary columns together in order to repair a broken column, to optimize a chemical separation by joining pieces of dissimilar column, to extend the column length by connecting two columns in series, and to add retention gaps or guard columns. In most analytical applications the column ends must also be connected to a sample injector and a detector.

The requirements placed upon a practical capillary connector for general use in chromatography applications are most demanding. The connector must be usable in regular contact with chemically reactive substances and organic solvents. It must remain leak-free when operated at internal pressures from zero (absolute) to several thousand pounds per square inch. It must not leak whether the fluid in the capillary be a liquid, a gas or a supercritical fluid. The fluid seal provided by the connector must be stable over temperature cycles from sub-ambient to several hundred degrees Celsius. The thermal mass must be small and the thermal conductivity high to maintain thermal equilibrium between the column and its immediate surroundings. In order to avoid degrading the separating power of the capillary columns, the connector must also contribute very little extra volume to the sample flow path and must avoid physical features that might contribute to turbulence and mixing in the fluids. It must make only a negligible contribution to the resistance to fluid flow in the column/injector/detector assembly. Finally, as a matter of convenience, the connection should be easily made without special tools and should be reusable.

In the past, many connectors have been devised to address the need for providing a fluid tight coupling between two capillary column ends. Some such connectors employ a ferrule with a longitudinal bore therethrough for inserting the ends of the columns to be coupled together, and a compression fitting for mechanically compressing the ferrule in order to provide a fluid tight seal between the inner bores of each column end. Another connector employs a cylindrical body with a longitudinal throughbore for receiving the ends of the capillary columns to be joined in a butt connection, and a polyimide sealing resin which is applied to the external joint between each column and the adjacent end wall of the connector in order to seal each column to the connector body. This usually requires heat curing of the resin for a minimum period of time, approximately 20 minutes. Still another connector consists of a hollow glass tube having a double conical configuration formed by forming elongated bulbs in an initially cylindrical tube at appropriate intervals (e.g. 1 cm), the resulting connector having a double-tapered internal bore narrowing from the two outer ends to the central portion thereof. In use, each column end is inserted into a different one of the ends of the connector and moved into a press-fit position. Press-fit glass tubes have also been used with a ferrule and compression fitting at each end to seal against the capillary column.

Known connectors suffer from several disadvantages. The ferrule and compression style connectors require several moving parts and must be carefully assembled and reassembled. Many require separate elastomeric seals to ensure fluid-tight connection. When a ferrule is used, a small piece of column must be cut off after the column is inserted into the ferrule to eliminate debris that might have been forced into the bore of the capillary column. Also, all parts must be chemically inert to the substances used in the analytical chromatographic process and must exhibit good temperature stability. This increases the cost of such connectors. The cylindrical body type connector suffers from the disadvantage of requiring a minimum finite curing time for the resin adhesive in order to provide the requisite fluid seal. In addition, care must be taken in applying the polyimide resin to ensure that no gaps or cracks exist in the adhesive, that the adhesive thoroughly covers the joint to be sealed and that the adhesive does not enter into the lumen of the capillary. In addition, this type of connector cannot be readily reused once the seals have ruptured, or one or more of the capillaries have broken or cracked. The drawn glass double conical connector of the pressfit variety has been reported to suffer from inconsistent fluid seal, particularly with modern high temperature fused silica capillary columns. After heating to elevated temperatures, connections have been observed to begin leaking and the fused silica butts can be either pushed further into the seat or removed therefrom. This had not previously been possible because short term heating above about 200° C. caused the lower temperature polyimide coating on the exterior of the fused silica column to stick so firmly to the connector wall that pulling the connection apart with brute force resulted in the breakage of the fused silica at the seal. Thus, the need exists for a relatively simple column connector devoid of the disadvantages of known devices.

SUMMARY OF THE INVENTION

The invention comprises a capillary connector which is extremely simple in design and construction, and thus inexpensive to manufacture, requires no elastomeric fluid seal, is designed to allow repeated connect/disconnect cycles and to make the connect and disconnect operations quick and easy, and which provides the desirable characteristics of good temperature stability, low dead volume, chemical inertness, and the ability to seal against moderate gas and liquid pressures.

In its broadest aspect, the invention comprises a body member, preferably having cylindrical geometry, the body member having a first end and a second end and an internal bore extending between the first and second ends, preferably tapered therealong, and dimensioned to receive an end portion of a capillary column in fluid sealing relation therewith. One of the first and second ends of the body member has a radiussed surface capable of slight deformation when brought into contact with a second connector surface to provide a fluid seal therebetween without the need for a sealing gasket. The second connector surface may be flat or radiused.

The body member is fabricated from a material having high compressive strength, resiliency and inertness to chromatographic substances, the material preferably comprising zirconia.

The internal bore of the body member is optionally provided with an uneven surface portion, such as a microgrooved portion, for promoting adherence of an adhesive or potting compound for retaining the end portion of the capillary column therein.

The individual connectors can be used in pairs as part of a connector assembly for providing a sealed fluid coupling between a pair of capillary columns. The assembly includes means for maintaining the pair of body members in mutual alignment with a radiussed surface of each body member in sealing contact. The maintaining means preferably comprises a split sleeve covering the ends of the pair of body members, and means for applying a biasing force urging the pair of body members into facing contact, the biasing force preferably being of sufficient magnitude to deform the confronting radiussed surfaces of each of the body members.

The individual connectors can also be used in combination with a male or female portion of an injector body or liner having a flat or radiused face capable of coacting with the connector to provide the requisite deformation and fluid seal.

In some applications in which the use of a capillary column holder such as a collet is preferred, a body member may be provided with attachment means for enabling attachment of such a capillary column holder, the attachment means preferably comprising an external threaded portion of the body member adjacent one of the ends thereof.

In use, an end of a first capillary column is inserted into the internal bore of the body member to a press-fit. For capillary columns coated with a protective polymer outer layer, such as fused silica columns, this creates a seal between the column end and the internal bore. The capillary may be anchored into the body member in a permanent position, if desired, by applying a suitable adhesive, such as a glue or an epoxy resin. For a removable column installation, a column holding device, such as a collet, can be mounted to the body member by securing the collet or holder to the attachment means. A second column to be coupled to the first column is similarly installed in another body member, after which the two body members are aligned together by means of the split sleeve. The two body members are then compressed together so that the confronting radiussed surfaces deform and flatten out to create a fluid seal about the internal bores without the need for a separate sealing gasket.

In order to ensure sufficient biasing force to compress the radiussed surfaces, a bias force applying mechanism can be installed on the two body members.

For a fuller understanding of the nature and advantages of the invention, reference should be had to the ensuing detailed description taken in conjunction with the accompanying drawings.

DETAILED DESCRIPTION OF THE PREFERRED EMBODIMENTS

Figure 1:
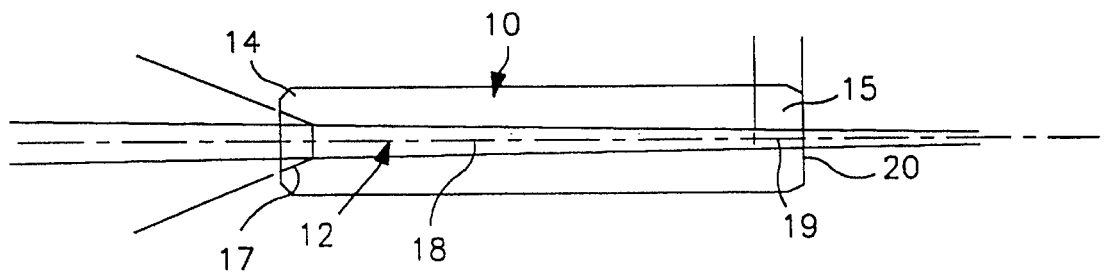
FIG. 1 is a sectional view of a single connector incorporating the invention.

Turning now to the drawings, FIG. 1 is a sectional view illustrating a preferred embodiment of a single body member fabricated according to the teachings of the invention. As seen in this figure, a body member generally designated with reference numeral 10 has a compound longitudinally extending bore generally designated with reference numeral 12 extending between the ends 14, 15 thereof. Body member 10 is fabricated from a molded ceramic material or a glass having a high compressive strength, resiliency and inertness to chromatographic substances. Zirconia is the preferred one of such materials; fused silica is another suitable equivalent. Other materials may also prove to be suitable for use in forming body member 10. In general, candidate materials must be relatively inert, must undergo reversible deformation under pressure in the region of contact and must have sufficient strength to avoid cracking under the pressure required to achieve a fluid seal.

Longitudinal bore 12 has a flared entry portion 17 adjacent end 14 to facilitate insertion of the end of a capillary column in the manner described below. The major length 18 of longitudinal bore 12 is tapered as illustrated inwardly in the direction of end 15. The remainder of longitudinal bore 12 is a portion 19 of essentially constant diameter. The value of the diameter of portion 19 should be less than that of the minimum outer diameter of a capillary column to be received within bore 12. In a specific embodiment of body member 10, the diameter of portion 19 is 0.01000 inch plus or minus 0.0005 inch; and the length of portion 19 is 0.050 inch. For the specific body member 10, the total angle subtended by flared opening portions 17 of bore 12 is 40° plus or minus 3°, while the total angle subtended by the tapered portion 18 is 3.0° plus or minus 0.5°. Other specific dimensions will apply to other applications of the invention.

Tapered section 18 is dimensioned to ensure an interference fit between the outer diameter of the inserted end of a capillary column and the wall surface of portion 18 of bore 12 at some point along the surface, preferably adjacent the inner end of portion 19.

A significant aspect of the configuration of body member 10, which is not evident from FIG. 1, is the contour of inner surface 20 of body member 10. Specifically, surface 20 is formed with a positively radiussed surface centered about the axis of bore portion 19. For the specific body member 10 having an outer diameter in the range between 2.4985 and 2.4995 mm, the radius of curvature is 20 mm measured along the axis of bore portion 19. The purpose for this positive radius is described below.

Figure 2:
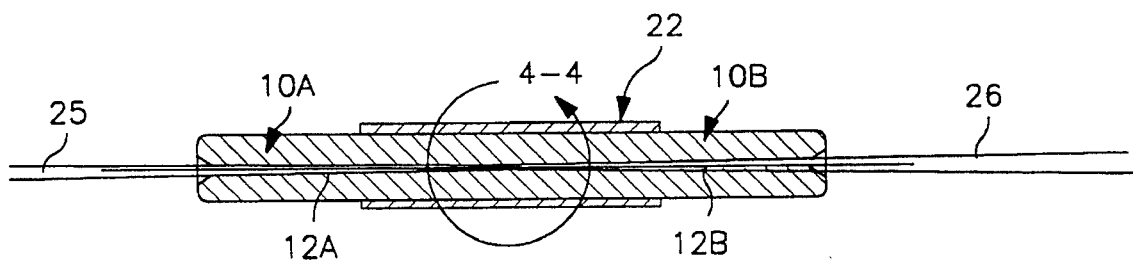
FIG. 2 is a sectional view showing two such connectors aligned together by a split sleeve with capillary columns installed.
Figure 3:
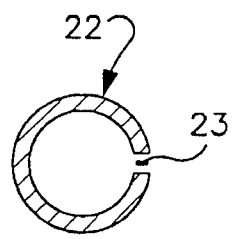
FIG. 3 is an end view of the split sleeve.

With reference to FIG. 2, a pair of body members 10A, 10B are seen aligned in an axially concentric fashion by means of a split sleeve 22. Split sleeve 22 is a generally cylindrical member having a longitudinal slot 23 (FIG. 3)

and an inner diameter slightly smaller than the outer diameter of body members 10A, 10B. When installed as shown in FIG. 2, split sleeve 22 provides a slight compressive force essentially radially inwardly of members 10A, 10B in order to hold members 10A, 10B in body alignment, with bores 12A, 12B essentially coaxially arranged as illustrated. Also illustrated in FIG. 2 are portions of a pair of capillary columns 25, 26 with end portions installed in the bores 12A, 12B of body members 10A, 10B. In the example shown in FIG. 2, each capillary column 25, 26 is press-fitted into the corresponding bore 12A, 12B without any additional provision for securing the column within the bore. For those applications requiring additional securing force, a suitable adhesive may be applied between the outer surface of one or both capillary columns 25, 26 and the wall surface of one or more bores 12A, 12B. To facilitate adhesion, the wall surface of a given bore 12 may be provided with an uneven portion, for example by forming small grooves therein to provide pockets for the adhesive. In addition to microgrooves, the bore surface may be textured or randomly scored for the same purpose.

Figure 4:
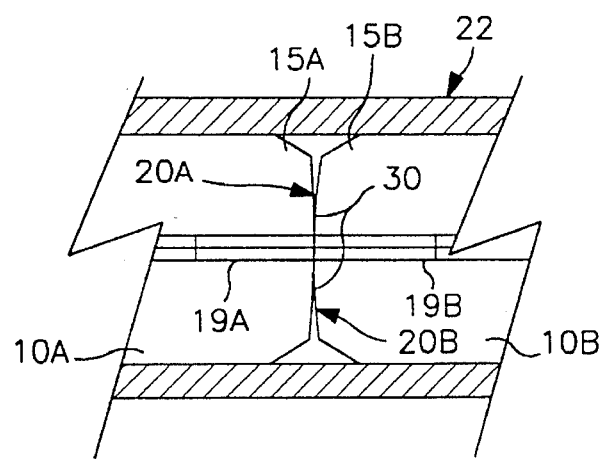
FIG. 4 is an enlarged detail view illustrating the radiussed surface compression.

With reference to FIG. 4, when two body members 10A, 10B are aligned with their faces 20A, 20B in mutual contact, longitudinal bore portions 19A, 19B are aligned to provide a through passage therebetween. Most importantly, when a biasing force is applied to body members 10A, 10B in such a manner as to force members 10A, 10B against one another, the radiussed surfaces 20A, 20B deform and form a fluid sealing region 30 about bore portions 19A, 19B. This fluid sealing region 30 may have an irregular contour; however, it is only necessary that the region totally surround the bore openings in end faces 20A, 20B. The exact shape and extent of sealing region 30 will depend upon the magnitude of the biasing forces and the resiliency of the material.

Figure 5:
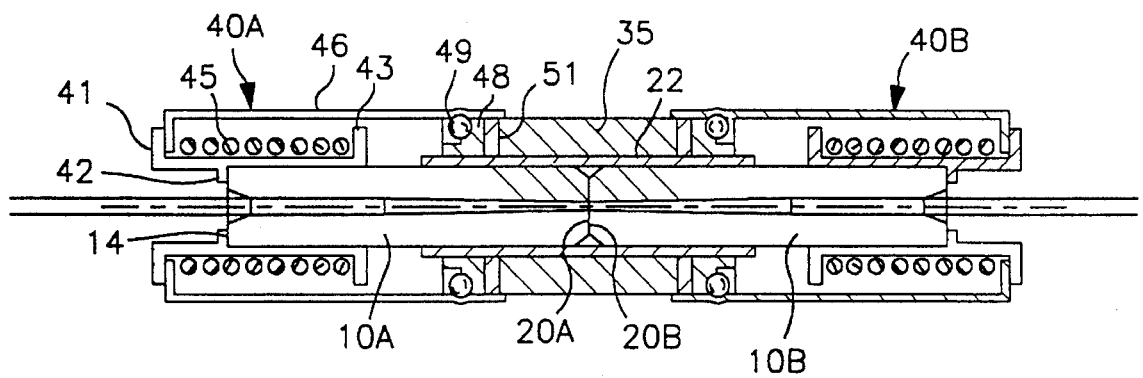
FIG. 5 is a sectional view of an assembly of the invention.

While in some applications manual biasing force may be applied to opposite ends of body members 10A, 10B of sufficient magnitude to deform the end faces 20A, 20B to provide the sealing region 30, with split sleeve 22 providing sufficient frictional force to hold body members 10A, 10B together in the deformed relationship, in many applications it will be preferable or necessary to provide additional biasing means to maintain the body member faces in the deformed, fluid sealing state. FIG. 5 illustrates one such arrangement which includes an annular sleeve housing 35 received about split sleeve 22 and a pair of symmetrically arranged bias force providing mechanisms generally designated with reference numerals 40A, 40B, respectively. With reference to mechanism 40A, a spool-shaped inner member 41 includes an inwardly directed rib 42 for transferring a translatory force to the right as viewed in FIG. 5 to body member 10A. Rib 42 may comprise one or more teeth-like members, a single circular rib or a plurality of arcuate ribs. A radially outwardly directed spring stop flange 43 provides an inner stop for a bias spring 45 mounted about the outer circumference of inner member 41. An outer housing 46 is rotatably attached to an annular support member 48 by means of a plurality of ball bearings 49. Support member 48 is friction fitted over split sleeve 22 and is provided with a wave spring 51 to produce a radially outward bias force on the ball bearings 49.

To install, sleeve housing 35 is arranged about split sleeve 22, wave spring 51 is arranged about one end of split sleeve 22, followed by support member 48 and housing 46 of assemblies 40A, 40B. As assembly 40A is maneuvered to the right (and assembly 40B is maneuvered toward the left), the outer end 14 of body member 10A is contacted by rib 42. Continued axial motion toward the confronting surfaces 20A, 20B causes spool 43 to move axially outwardly, compressing spring 45 and providing sufficient axially inwardly directed force to maintain surfaces 20A, 20B in the compressed, deformed state. Upon release, surfaces 20A, 20B relax to the radiussed configurations due to the resiliency of the material from which body members 10A, 10B are fabricated.

One of the significant advantages of the invention is the ability of the radiussed surfaces 20A, 20B to provide a fluid-tight seal around the bore portions 19A, 19B when the radiussed surfaces 20A, 20B are compressed together and deform. This eliminates the need for a sealing gasket, and thus eliminates problems with gasket misalignment and deterioration with time, extreme temperature variations and exposure to solvents, diluents and other chromatographic substances. In addition, body members 10 are extremely simple in construction, durable in use and relatively inert to chemical substances. The assembly is relatively simple to assemble, and capillary columns can be easily inserted and removed (for removable applications) from the longitudinal bores 12 of the body members 10.

Figure 6:
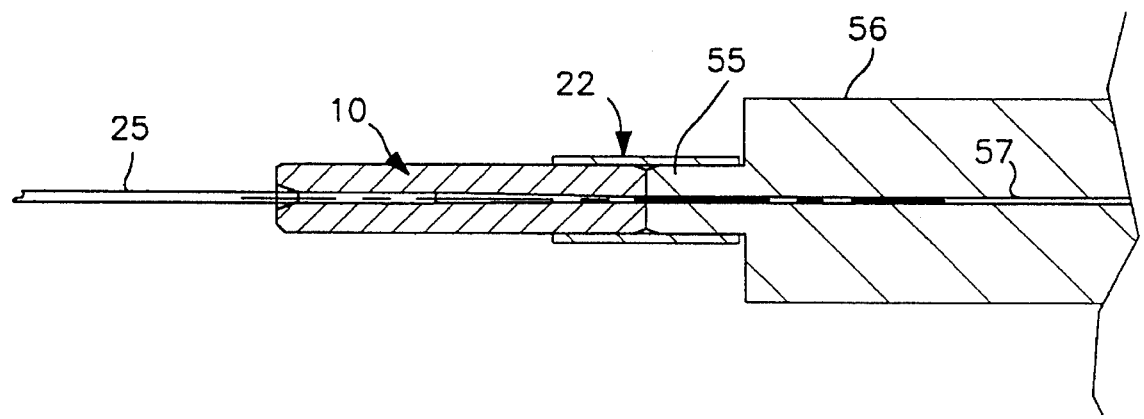
FIG. 6 is a sectional view showing a FIG. 1 connector coupled to a portion of an analytical instrument;.

The invention can be applied to form inter-capillary connections in the manner illustrated in FIGS. 2–5 or to provide connections between a capillary column and an injector liner, a detector insert or other appropriate instrument components. For example, as shown in FIG. 6, body member 10 may be attached by means of split sleeve 22 to an apertured projecting portion 55 of an injector body 56 having a flow channel 57.

Figure 7:
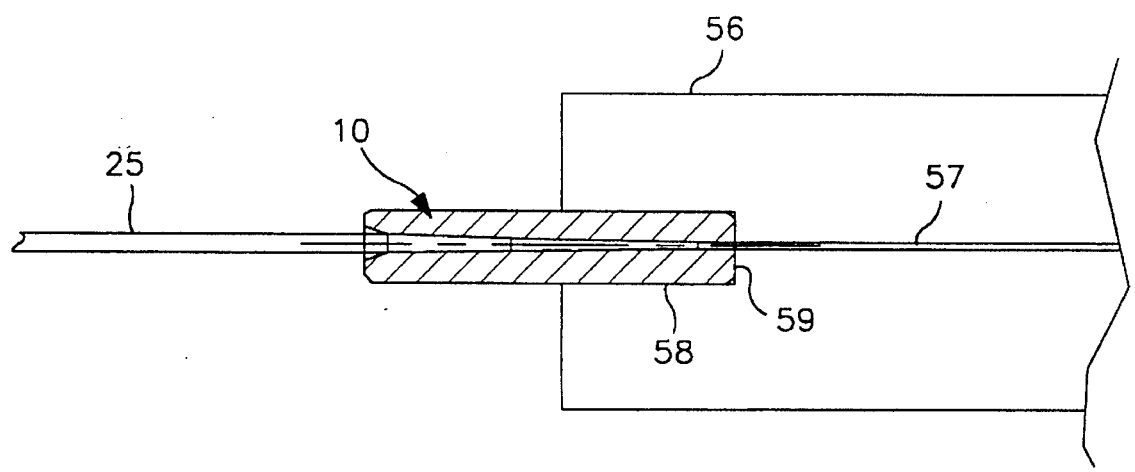
FIG. 7 is a sectional view similar to FIG. 6 illustrating use of the invention in a recessed opening for an analytical instrument.

Similarly, as illustrated in FIG. 7, body member 10 may be connected to an aperture recessed portion 58 of an injector body 56 having a flow channel 57. A positive attachment mechanism may be used to provide inward bias for member 10 into recessed portion 58.

In addition, body members formed of different materials may be paired, such as a body member 10A formed of zirconia and a body member 10B formed of silica, so long as the compressive strengths and resiliencies of the two different materials are sufficiently compatible to form the requisite fluid seal.

Figure 8:
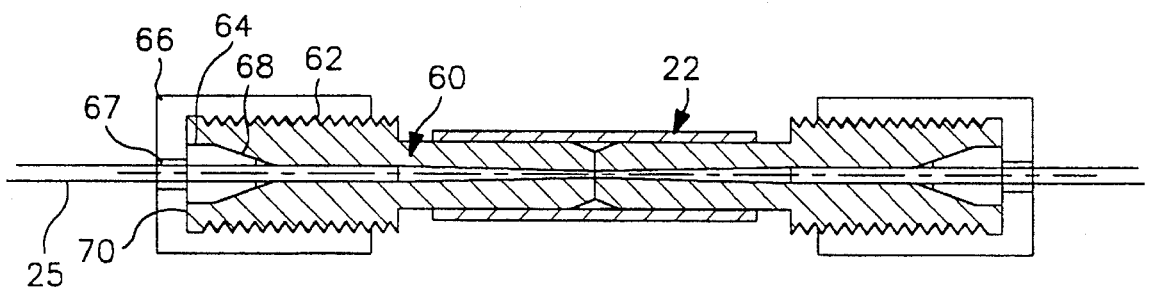
FIG. 8 is a sectional view of an alternate assembly.

FIG. 8 illustrates an alternate arrangement for mechanically attaching a capillary column to the body member. As seen in this figure, a body member 60 is provided with an enlarged externally threaded portion 62. A compressible ferrule 64 fabricated from any suitable material is received about the outer surface of a capillary column 25. An internally threaded cap 66 having an enlarged throughbore 67 for accommodating the outer diameter of capillary column 25 is threadably attached to portion 62 of body member 60. This arrangement functions in a conventional way to compress ferrule 64 as cap 66 is threaded onto portion 62 of body member 60. In particular, the tapered nose portion of ferrule 64 is received within a flared opening 68 to provide a seal therebetween as ferrule 64 is compressed by the inner surface 70 of threaded cap 66.

Figure 9:
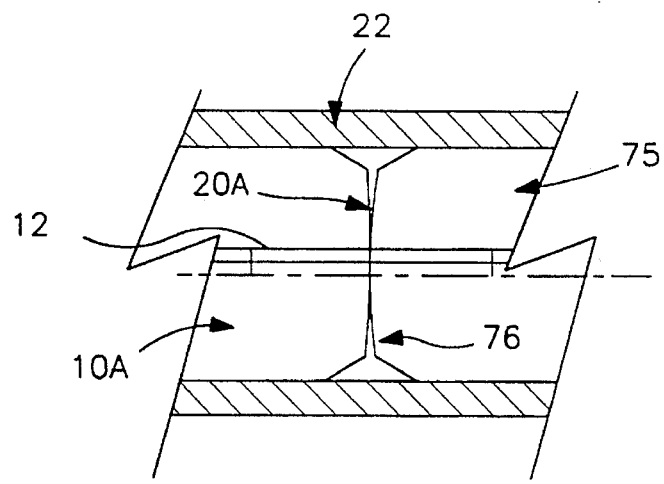
FIG. 9 is an enlarged detail view illustrating radiused surface compression between a radiused surface connector and a flat surface connector.

Although the invention has been described above with reference to body members 10A, 10B each having positively contoured confronting surfaces 20A, 20B, in some applications a body member 10 having a flat surface may be employed in combination with a body member having a positively radiussed surface as illustrated in FIG. 9. In particular, FIG. 9 illustrates a body member 10A having a positively radiussed end surface 20A in contact with a body member generally designated with reference numeral 75 and having a flat surface 76 formed substantially perpendicular to the bore axis 12. As will be appreciated by those skilled in the art, body member 75 may comprise either an independent body member or a portion of an injector liner, a detector insert or an injector body. Also, flat surface 76 may comprise surface 59 of recessed portion 58 of the FIG. 7 embodiment.

While the above provides a full and complete disclosure of the invention various modifications, alternate constructions and equivalents will occur to those skilled in the art. For example, while body member 10 has been described with reference to right circular cylindrical geometry, other geometrical configurations may be suitable for certain applications. Also, other bias force mechanisms, such as simple clamps, may be employed, as desired. Therefore, the above should not be construed as limiting the invention, which is defined by the appended claims.

What is claimed is:

1. A connector for fluid coupling a capillary column to a connection device having an internal fluid path and a connection surface, said connector comprising:

a body member formed from a material having a high compressive strength, resiliency and inertness to chromatographic substances,, said body member having a first end and a second end, an internal bore extending between said first and second ends and dimensioned to receive an end portion of a capillary column in fluid sealing relation therewith even in the absence of any externally caused deformation of the body member, one of said first and second ends of said body member having a curved surface with a region thereof capable of slight deformation when brought into contact with the connection surface to provide a fluid seal therebetween without the need for a sealing gasket.

2. The invention of claim 1 wherein said material is ceramic.

3. The invention of claim 1 wherein said body member is formed from zirconia.

4. The invention of claim 1 wherein said body member is formed from silica.

5. The invention of claim 1 wherein said internal bore is tapered along a portion thereof to enable an interference fit between said end portion of said capillary column said internal bore.

6. The invention of claim 1 wherein said body member has cylindrical geometry.

7. The invention of claim 1 wherein said curved surface has a positive radius of curvature.

8. The invention of claim 1 wherein said internal bore has an uneven surface portion for promoting adherence of an adhesive for retaining said end portion of said capillary column therein.

9. The invention of claim 1 further including a capillary column having an end portion received within said internal bore in fluid sealing relation therewith.

10. The invention of claim 9 further including an adhesive material within said internal bore for promoting said fluid sealing relation and retention of said end portion of said capillary column within said internal bore.

11. The invention of claim 1 wherein said body member is provided with attachment means for enabling attachment of a capillary column holder thereto.

12. The invention of claim 11 wherein said attachment means comprises an external threaded portion of said body member.

13. The invention of claim 12 wherein said external threaded portion is located adjacent the other one of said first and second ends of said body member.

14. A connector assembly for providing a sealed fluid coupling between a pair of capillary columns, said assembly comprising:

a pair of body members, each member having a first end and a second end, an internal bore extending between said first and second ends and dimensioned to receive an end portion of an associated capillary column in fluid sealing relation therewith even in the absence of any externally caused deformation of the body member, one of said first and second ends of at least one of said body members having a curved surface, at least one of said pair of body members being formed from a material having high compressive strength, resiliency and inertness to chromatographic substances; and means for maintaining said pair of body members in mutual alignment with said curved surface in sealing contact under slight deformation with a confronting end of the other one of said body members.

15. The invention of claim 14 wherein said material is ceramic.

16. The invention of claim 14 wherein said body member is formed from zirconia.

17. The invention of claim 14 wherein said body member is formed from silica.

18. The invention of claim 14 wherein said internal bore of each of said pair of body members is tapered along a portion thereof to enable an interference fit between said end portion of an associated capillary column and said internal bore.

19. The invention of claim 14 wherein at least one of said pair body member has cylindrical geometry.

20. The invention of claim 14 wherein said curved surface has a positive radius of curvature.

21. The invention of claim 14 wherein said internal bore of at least one said pair of body members has an uneven wall surface portion for promoting adherence of an adhesive for retaining said end portion of said capillary column therein.

22. A connector assembly for providing a sealed fluid coupling between a pair of capillary columns, said assembly comprising:

a pair of body members, each member having a first end and a second end, an internal bore extending between said first and second ends and dimensioned to receive an end portion of an associated capillary column in fluid sealing relation therewith, one of said first and second ends of at least one of said body members having a curved surface; and means for maintaining said pair of body members in mutual alignment with said curved surface in sealing contact under slight deformation with a confronting end of the other one of said body members, said maintaining means including a split sleeve covering the ends of said pair of body members.

23. The invention of claim 22 wherein said maintaining means further includes means for applying a biasing force urging said pair of body members into facing contact.

24. The invention of claim 22 wherein said maintaining means further includes means for applying a biasing force urging said pair of body members into facing contact of sufficient magnitude to deform said curved surface.

25. The invention of claim 14 further including at least one capillary column having an end portion received within said internal bore of at least one of said pair of body members in fluid sealing relation therewith.

26. The invention of claim 23 further including an adhesive material within said internal bore for promoting said fluid sealing relation and retention of said end portion of said at least one capillary column within said internal bore.

27. The invention of claim 14 further including a pair of capillary columns each having an end portion received within said internal bore of the associated one of said pair of body members in fluid sealing relation therewith.

28. The invention of claim 27 further including an adhesive material within each said internal bore of said pair of body members for promoting said fluid sealing relation and retention of said end portion of said capillary column within said internal bore.

29. The invention of claim 14 wherein at least one of said pair of body members is provided with attachment means for enabling attachment of a capillary column holder thereto.

30. The invention of claim 29 wherein said attachment means comprises an external threaded portion of said at least one of said pair of body members.

31. The invention of claim 30 wherein said external threaded portion is located adjacent the other one of said first and second ends of said at least one of said pair of body members.

32. The invention of claim 14 wherein each of said body members has a curved surface.

33. The invention of claim 14 wherein the confronting end of the other one of said body members is substantially flat.

34. The invention of claim 14 wherein one of said body members is a portion of an analytical instrument; and wherein said internal bore of said one of said body members has an internal diameter substantially equal to the inner diameter of the capillary column associated to the other one of said body members.

35. The invention of claim 34 wherein said portion of an analytical instrument comprises an injector body.

36. The invention of claim 34 wherein said portion of an analytical instrument comprises an injection liner.

\* \* \* \* \*